US009839405B2

United States Patent
Kim et al.

(10) Patent No.: US 9,839,405 B2
(45) Date of Patent: Dec. 12, 2017

(54) X-RAY IMAGING APPARATUS AND CONTROL METHOD THEREOF

(71) Applicant: SAMSUNG ELECTRONICS CO., LTD., Suwon-si (KR)

(72) Inventors: Sung Su Kim, Yongin-si (KR); Hyun Hwa Oh, Hwaseong-si (KR); Jae Hyun Kwon, Hwaseong-si (KR); Young Hun Sung, Hwaseong-si (KR); Kang Eui Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 261 days.

(21) Appl. No.: 14/621,451

(22) Filed: Feb. 13, 2015

(65) Prior Publication Data

US 2015/0297163 A1    Oct. 22, 2015

(30) Foreign Application Priority Data

Apr. 17, 2014    (KR) .................. 10-2014-0045873

(51) Int. Cl.
*A61B 6/04*    (2006.01)
*A61B 6/00*    (2006.01)
*H04N 5/32*    (2006.01)

(52) U.S. Cl.
CPC .......... *A61B 6/5217* (2013.01); *A61B 6/0414* (2013.01); *A61B 6/502* (2013.01); *H04N 5/32* (2013.01)

(58) Field of Classification Search
CPC ..... A61B 6/5217; A61B 6/502; A61B 6/0435; H04N 5/32; G06T 7/0014; G06T 15/08; G06T 2207/10081; G06T 2207/30068
USPC .......................................................... 378/37
See application file for complete search history.

(56) References Cited

U.S. PATENT DOCUMENTS

| 2011/0026791 A1* | 2/2011 | Collins ................. G06K 9/62 382/131 |
| 2012/0063566 A1* | 3/2012 | Smith ................... A61B 6/025 378/37 |

* cited by examiner

*Primary Examiner* — Courtney Thomas
(74) *Attorney, Agent, or Firm* — Sughrue Mion, PLLC

(57) ABSTRACT

Disclosed herein are an X-ray imaging apparatus for providing information about accurate breast density, and a control method of the X-ray imaging apparatus. The X-ray imaging apparatus includes a reconstructing unit configured to reconstruct volumes relating to an object from an X-ray image of the object, a first reference image of the object generated based on the object being of only adipose tissue, and a second reference image of the object generated based on the object being of only fibroglandular tissue, and a density calculator configured to calculate a density of the object that is a ratio of fibroglandular tissue of the object with respect to entire tissue of the object using the reconstructed volumes of the object.

18 Claims, 18 Drawing Sheets

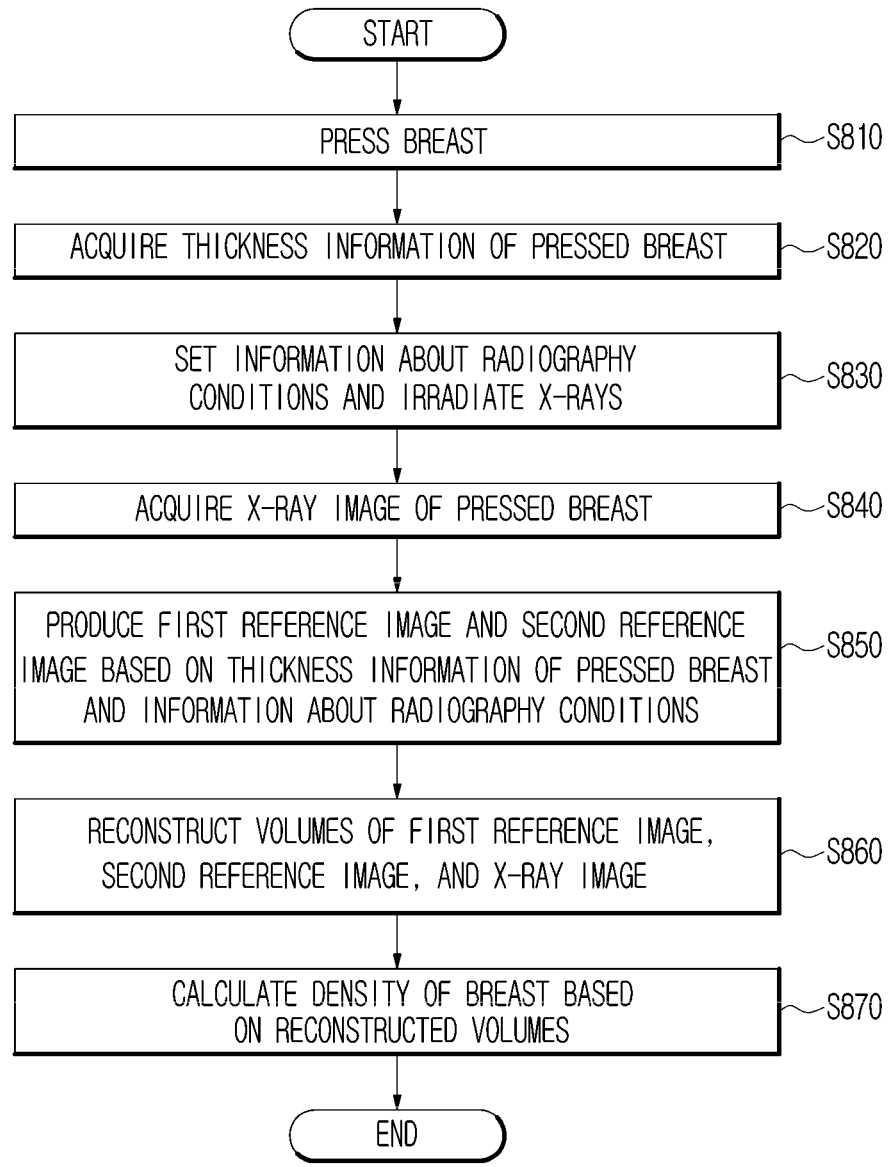

X-RAY IMAGING APPARATUS AND CONTROL METHOD THEREOF

CROSS-REFERENCE TO RELATED APPLICATION

This application claims priority from Korean Patent Application No. 10-2014-0045873, filed on Apr. 17, 2014 in the Korean Intellectual Property Office, the disclosure of which is incorporated herein by reference in its entirety.

BACKGROUND

1. Technical Field

Apparatuses and methods consistent with exemplary embodiments relate to an X-ray imaging apparatus and a control method thereof, and more particularly, to an X-ray imaging apparatus for providing information about accurate breast density, and a control method of the X-ray imaging apparatus.

2. Description of the Related Art

An X-ray imaging apparatus is an imaging apparatus for acquiring images of the inside of an object, such as a human body or another item, by irradiating X-rays toward the object. Because the X-ray imaging apparatus can show the inside structure of an object, it is widely used in the medical field to detect abnormal tissue, such as lesions, inside a human body or to understand the inside structure of an object or a component. Also, the X-ray imaging apparatus may be used to check the inside of baggage at airports.

AN X-ray imaging apparatus may include Digital Radiography (DR), Computed Tomography (CT), and Full Field Digital Mammography (FFDM).

The operating principles of the X-ray imaging apparatus are as follows. The X-ray imaging apparatus irradiates X-rays toward an object, such as a human body, another element, item, or component, then receives the X-rays that were able to propagate through the object and/or any that were not transmitted through the object, converts the received X-rays into electrical signals, and reads out the electrical signals to produce an X-ray image. The X-ray image is displayed on a display unit so that a user can see the inside structure of the subject.

SUMMARY

Therefore, it is an aspect of the present disclosure to provide an X-ray imaging apparatus for providing information about accurate breast density, and a control method of the X-ray imaging apparatus.

Additional aspects of the disclosure will be set forth in part in the description which follows and, in part, will be obvious from the description, or may be learned by practice of the disclosure.

In accordance with an aspect of an exemplary embodiment, there is provided an X-ray imaging apparatus including a reconstructing unit configured to reconstruct volumes relating to an object from an X-ray image of the object, a first reference image of the object generated based on the object being of only adipose tissue, and a second reference image of the object generated based on the object being of only fibroglandular tissue, and a density calculator configured to calculate a density of the object that is a ratio of fibroglandular tissue of the object with respect to entire tissue of the object using the reconstructed volumes of the object.

The X-ray imaging apparatus may further include a pressure paddle disposed between an X-ray source assembly and an X-ray detection assembly and configured to press the object, a first reference image producer configured to produce the first reference image based on thickness information of the pressed object and an X-ray attenuation coefficient of adipose tissue, and a second reference image producer configured to produce the second reference image based on the thickness information of the pressed object and an X-ray attenuation coefficient of fibroglandular tissue.

The X-ray imaging apparatus may further include a driver configured to move the pressure paddle in an up direction and down direction, a rotation angle sensor configured to detect a rotation angle of the driver, and a thickness calculator configured to calculate the thickness information of the pressed object based on the rotation angle detected by the rotation angle sensor.

The X-ray imaging apparatus may further include a thickness corrector configured to correct the thickness information calculated by the thickness calculator, based on a size of the object and a compression force applied to the object.

The X-ray imaging apparatus may further include a size calculator configured to calculate the size of the object based on a distance between a center point of an object area detected from the X-ray image, and a center point of the driver.

The X-ray imaging apparatus may further include a compression force sensor disposed on a lower surface of the pressure paddle, and configured to detect the compression force applied to the object.

The X-ray imaging apparatus may further include a distance sensor array disposed in a lower portion of the X-ray source assembly, and configured to detect a distance to the pressure paddle, and a thickness calculator configured to calculate the thickness information of the pressed object based on the distance detected by the distance sensor array.

The X-ray imaging apparatus may further include an interpolator configured to interpolate the distance detected by the distance sensor array.

The reconstructing unit may be further configured to reconstruct the volumes relating to the object from the X-ray image, the first reference image, and the second reference image, respectively, based on the thickness information of the pressed object and information about radiography conditions of the X-ray image.

The information about the radiography conditions may include at least one of information about a tube voltage, information about tube current, information about a filter, and information about an X-ray source.

The density calculator may be further configured to calculate the density based on a difference between the volume of the object reconstructed from the X-ray image and the volume of the object reconstructed from the first reference image.

According to an aspect of another exemplary embodiment, there is provided a control method of an X-ray imaging apparatus, including reconstructing volumes relating to an object from an X-ray image of the object, a first reference image of the object generated based on the object being of only adipose tissue, and a second reference image of the object generated based on the object being of only fibroglandular tissue, and calculating a density of the object that is a ratio of fibroglandular tissue of the object with respect to entire tissue of the object, using the reconstructed volumes of the object.

The control method may further include pressing the object using a pressure paddle disposed between an X-ray source assembly and an X-ray detection assembly, producing the first reference image based on thickness information of the pressed object and an X-ray attenuation coefficient of adipose tissue, and producing the second reference image based on the thickness information of the pressed object and an X-ray attenuation coefficient of fibroglandular tissue.

The control method may further include detecting a rotation angle of a driver configured to move the pressure paddle, using a rotation angle sensor, and calculating the thickness information of the pressed object based on the rotation angle detected by the rotation angle sensor.

The control method may further include correcting the calculated thickness information based on a size of the object and a compression force applied to the object.

The size of the object may be calculated based on a distance between a center point of an object area detected from the X-ray image, and a center point of the driver, and the compression force applied to the object may be detected by a compression force sensor disposed on a lower surface of the pressure paddle.

The control method may further include detecting a distance to the pressure paddle, using a distance sensor array disposed in a lower portion of the X-ray source assembly, and calculating the thickness information of the pressed object based on the distance detected by the distance sensor array.

The reconstructing the volumes relating to the object may include reconstructing the volumes relating to the object from the X-ray image, the first reference image, and the second reference image, respectively, based on the thickness information of the pressed object and information about radiography conditions of the X-ray image.

The calculating the density may include calculating a volume which is a difference between the volume of the object reconstructed from the second reference image and the volume of the object reconstructed from the X-ray image, and calculating the density based on a difference between the calculated volume and the volume of the object reconstructed from the first reference image.

BRIEF DESCRIPTION OF THE DRAWINGS

The above and/or other aspects of the disclosure will become apparent and more readily appreciated from the following description of exemplary embodiments, taken in conjunction with the accompanying drawings, in which:

FIG. 15 is a flowchart illustrating a control method of an X-ray imaging apparatus, according to an exemplary embodiment of the present disclosure.

DETAILED DESCRIPTION

Figure 1:
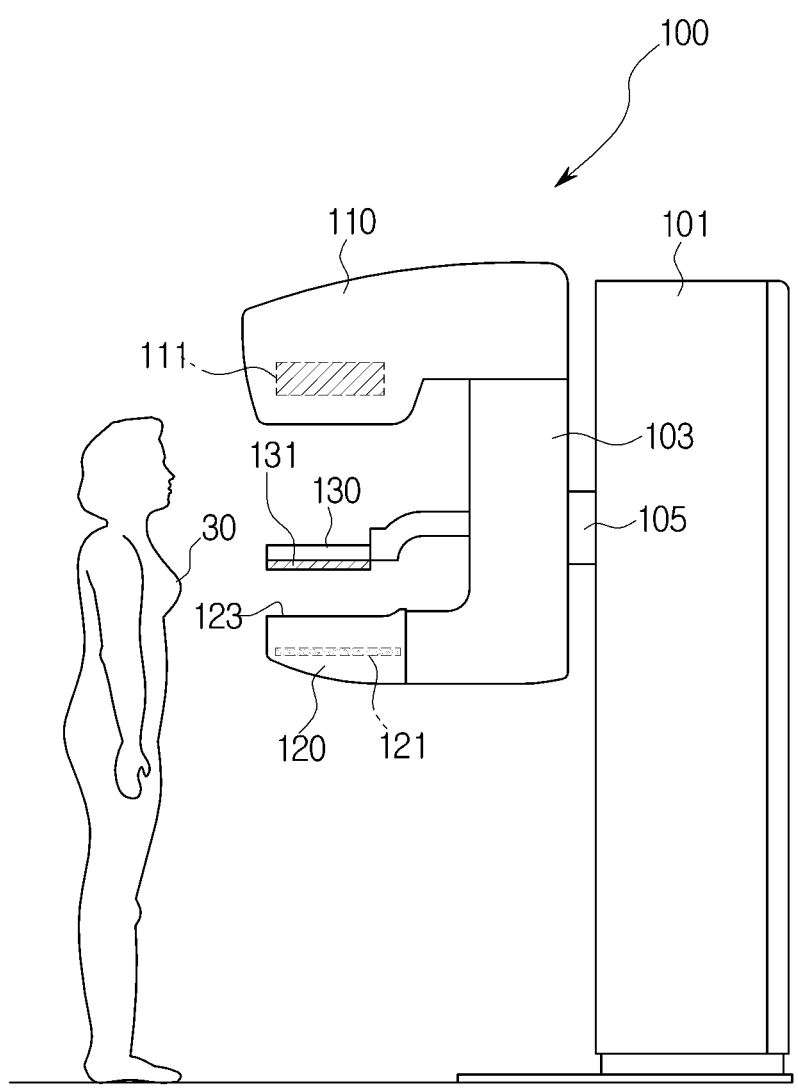
FIG. 1 illustrates an external appearance of an X-ray imaging apparatus according to an exemplary embodiment of the present disclosure.

Reference will now be made in detail to the exemplary embodiments of the present disclosure, examples of which are illustrated in the accompanying drawings, wherein like reference numerals refer to like elements throughout.

Hereinafter, an X-ray imaging apparatus and a control method thereof according to exemplary embodiments of the present disclosure will be described with reference to the appended drawings. Throughout the drawings, like reference numerals will be understood to refer to like components.

The X-ray imaging apparatus includes Digital Radiography (DR), Computed Tomography (CT), and Full Field Digital Mammography (FFDM). In the following description, the X-ray imaging apparatus is assumed to be FFDM.

FIG. 1 illustrates an external appearance of an X-ray imaging apparatus according to an exemplary embodiment of the present disclosure. As illustrated in FIG. 1, an X-ray imaging apparatus 100 may include a main body 101, a frame 103, an arm 105, an X-ray source assembly 110, an X-ray detection assembly 120, and a pressure paddle 130.

The arm 105 may connect the frame 103 to the main body 101. The arm 105 may be movable in an up direction and a down direction. An operator may move the arm 105 in the up and/or down directions to adjust a height of the frame 103. Also, the arm 105 may rotate within a predetermined angle range with respect to a coupling axis with the main body 101. If the arm 105 rotates at a predetermined angle, the frame 103 connected to the arm 105 may rotate at the predetermined angle accordingly.

The X-ray source assembly 110, the X-ray detection assembly 120, and the pressure paddle 130 may be installed by being attached to the frame 103. The X-ray source assembly 110 may face the X-ray detection assembly 120. The pressure paddle 130 may be positioned between the X-ray source assembly 110 and the X-ray detection assembly 120.

In the X-ray source assembly 110 may have an X-ray tube 111 installed within the X-ray source assembly 110, and the X-ray tube 111 may be configured to generate X-rays.

The X-ray detection assembly 120 may include a breast contact part 123 and an X-ray detector 121. The breast contact part 123 may be an upper surface part of the X-ray detection assembly 120 which a target breast contacts. In other words, the breast contact part 123 may be a part on which a breast is placed. The breast contact part 123 may be made of a material (for example, a carbon sheet) having excellent X-ray transmittance. The X-ray detector 121 may be installed in the X-ray detection assembly 120, and may be configured to detect X-rays transmitted through a breast among X-rays irradiated from the X-ray tube 111.

The pressure paddle 130 may press a breast placed on the breast contact part 123. In order to press the breast, the pressure paddle 130 may be movable in an up and down direction relative to the frame 103 and the X-ray detection assembly 120.

According to an exemplary embodiment, the pressure paddle 130 may be moved manually. In detail, an operator may hold the pressure paddle 130 or a handle provided on one side of the pressure paddle 130, and apply a force in an up and/or down direction to thereby move the pressure paddle 130 in the up or down direction.

According to another exemplary embodiment, the pressure paddle 130 may be moved automatically. In order to move the pressure paddle 130 automatically, the pressure paddle may be connected to a driver (190 of FIG. 2) to drive the pressure paddle 130 in the up-down direction. In this case, if the operator manipulates an input unit (150 of FIG. 5) to input a command for moving the pressure paddle 130 in the up-down direction, a control signal corresponding to the input command may be generated, and the generated control signal may be provided to the driver 190. Then, the driver 190 may be driven according to the control signal to move the pressure paddle 130 in the up-down direction.

The pressure paddle 130 may be made of a soft material. For example, the pressure paddle 130 may be made of plastic. If the pressure paddle 130 is made of a soft material, a breast may be prevented from being harmed or damaged when it is pressed by the pressure paddle 130.

After a breast is pressed by the pressure paddle 130 moved manually or automatically, thickness information of the breast may be acquired. This operation will be described with reference to FIG. 2, below.

Figure 2:
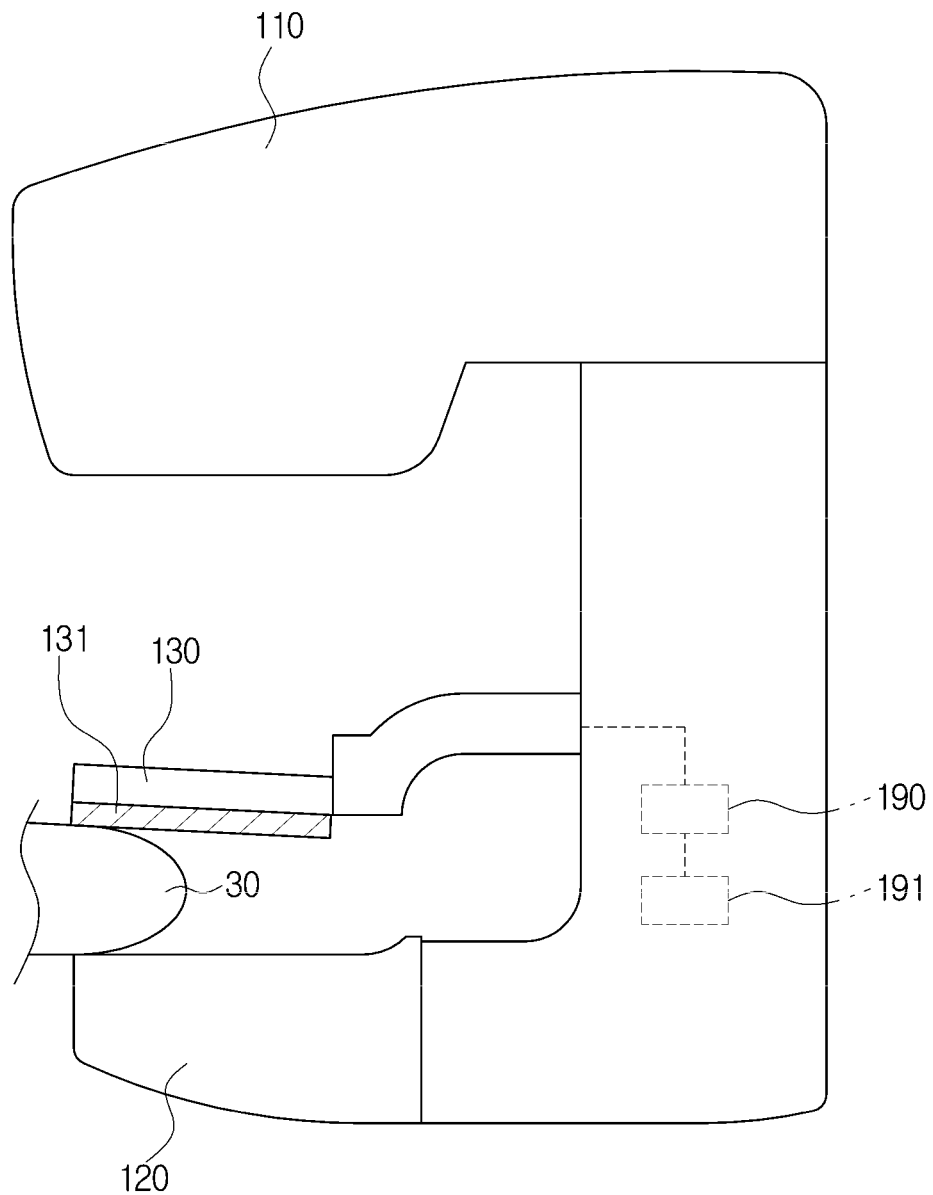
FIG. 2 is a view for illustrating a method of acquiring thickness information of a breast using an X-ray imaging apparatus, similar to that shown in FIG. 1, according to an exemplary embodiment of the present disclosure.

FIG. 2 is a view for describing a method of acquiring thickness information of a breast in the X-ray imaging apparatus 100 illustrated in FIG. 1.

As illustrated in FIG. 2, the pressure paddle 130 may be connected to the driver 190. The driver 190 may be used to move the pressure paddle 130 in the up-down direction. The driver 190 may be a motor, a vacuum pump, or a hydraulic pump. In the following description, the driver 190 is assumed to be a motor.

If the driver 190 is a motor, the motor may be connected to a rotation angle sensor 191 that is configured to detect a rotation angle of the motor. If a rotation angle of the motor is detected by the rotation angle sensor 191, thickness information of a pressed breast may be calculated based on the detected rotation angle. Specifically, by calculating a movement distance of the pressure paddle 130 based on the detected rotation angle, and then subtracting the movement distance of the pressure paddle 130 from a distance between the pressure paddle 130 and the breast contact part 123 before the pressure paddle 130 is moved, thickness information of the pressed breast may be acquired.

However, because the acquired thickness information of the breast corresponds to the thickness of a breast part placed furthest from the driver 190, the thickness information may be different from thickness information of the entirety of the breast. Specifically, due to the characteristic shape of a breast, the thickness of a breast part that is placed close to the driver 190 may be different from the thickness of a breast part that is placed furthest from the driver 190. However, the thickness information of the breast, acquired based on the rotation angle detected by the rotation angle sensor 191 corresponds to thickness information of a breast part placed further from the driver 190 as shown in FIG. 2. Accordingly, the thickness information of the breast may be corrected by calculating based on the rotation angle of the motor such that it approximates thickness information of the real breast. In order to correct the thickness information of the breast calculated based on the rotation angle of the motor, information about a compression force applied to the breast and information about a size of the breast are needed.

According to an exemplary embodiment, information about a compression force applied to the breast may be obtained by a compression sensor 131 installed on a lower surface, part, or portion of the pressure paddle 130. Information about a size of the breast may be obtained by analyzing an X-ray image for the pressed breast. A method of obtaining information about a size of a breast will be described in detail with reference to FIG. 9, later.

As illustrated in FIG. 2, after the breast is pressed by the pressure paddle 130, X-rays generated by the X-ray tube 111 of the X-ray source assembly 110 may be irradiated toward the pressed breast, and the X-rays transmitted through the pressed breast may be detected by the X-ray detector 121 of the X-ray detection assembly 120. As a result, an X-ray image for the pressed breast may be acquired.

As such, if X-rays are irradiated toward the breast while the breast is pressed by the pressure paddle 130, it is possible to acquire a clear X-ray image for the breast while exposing the breast to a smaller dose of X-rays.

Figure 3:
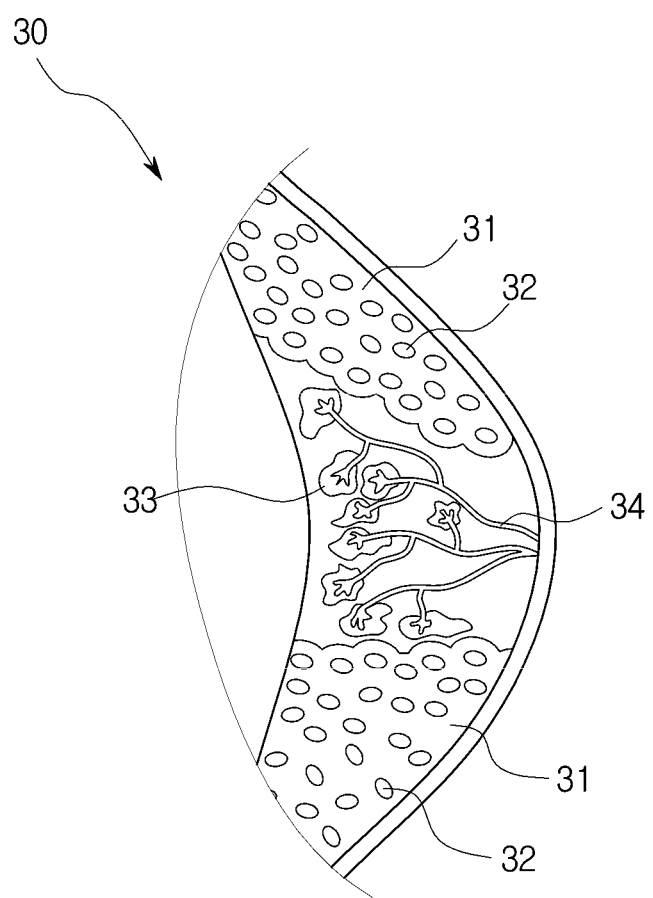
FIG. 3 illustrates an internal structure of a breast.

FIG. 3 illustrates an internal structure of a breast. Referring to FIG. 3, the inner tissue of a breast 30 may be comprised of fibrous tissue 31 surrounding the breast 30 and maintaining the shape of the breast 30, adipose tissue 32 distributed over the whole area of the breast 30, mammary tissue 33 to make breast milk, duct tissue 34 that are transfer ducts of breast milk, etc. Tissue, such as the mammary tissue 33 and the duct tissue 34, participating in making and supplying breast milk among the above-mentioned tissue is called fibroglandular tissue.

An attenuation coefficient is data representing a degree of X-ray attenuation when X-rays are transmitted through a material. Because different materials constituting an object have different attenuation coefficients, the inner structure of the object may be visualized based on degrees of X-ray transmission.

Figure 4:
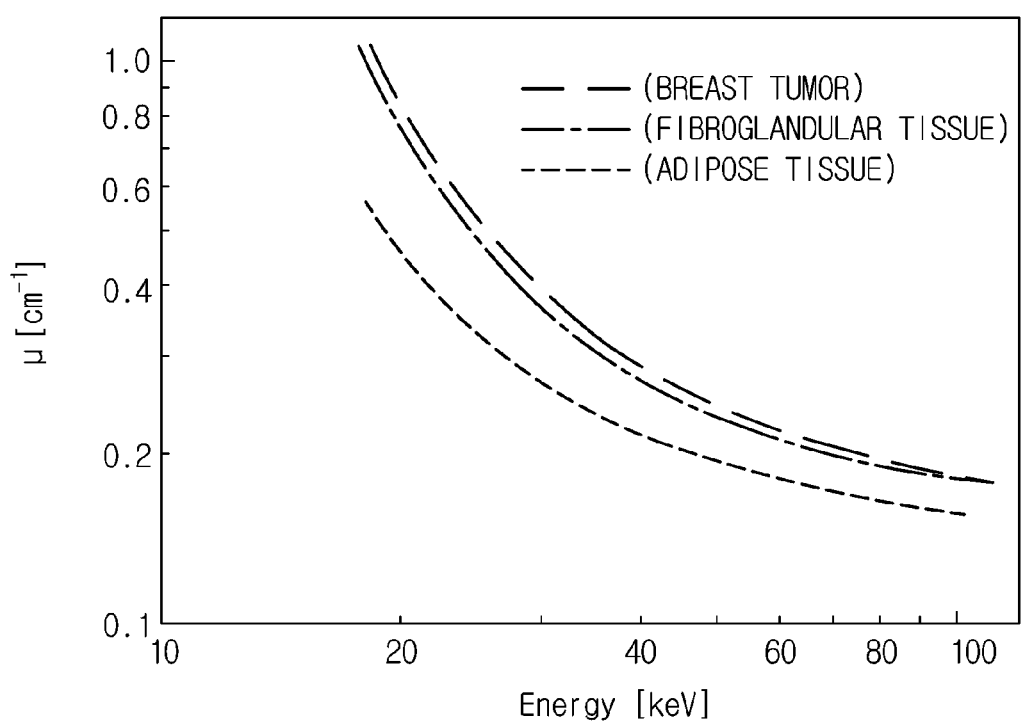
FIG. 4 is a graph showing attenuation coefficients with respect to energy bands for internal materials of a breast.

FIG. 4 is a graph showing attenuation coefficients with respect to energy bands for internal materials of a breast. Referring to FIG. 4, internal materials of a breast may include breast tumor, fibroglandular tissue, and adipose tissue.

As shown in FIG. 4, different materials constituting a breast have small attenuation coefficient differences. The reason is because a breast is composed of only soft tissues.

If the thickness of the breast is thinned by the pressure paddle 130, materials constituting the breast spread with respect to a direction in which X-rays are irradiated, without overlapping. As a result, an X-ray image having high quality, that is, a clear X-ray image can be obtained. In addition, a dose of X-rays to which the breast is exposed can be reduced.

The external appearance of the X-ray imaging apparatus 100 according to an exemplary embodiment of the present disclosure has been described with reference to FIGS. 1 to 4. Hereinafter, a configuration of the X-ray imaging apparatus 100 according to an exemplary embodiment of the present disclosure will be described.

Figure 5:
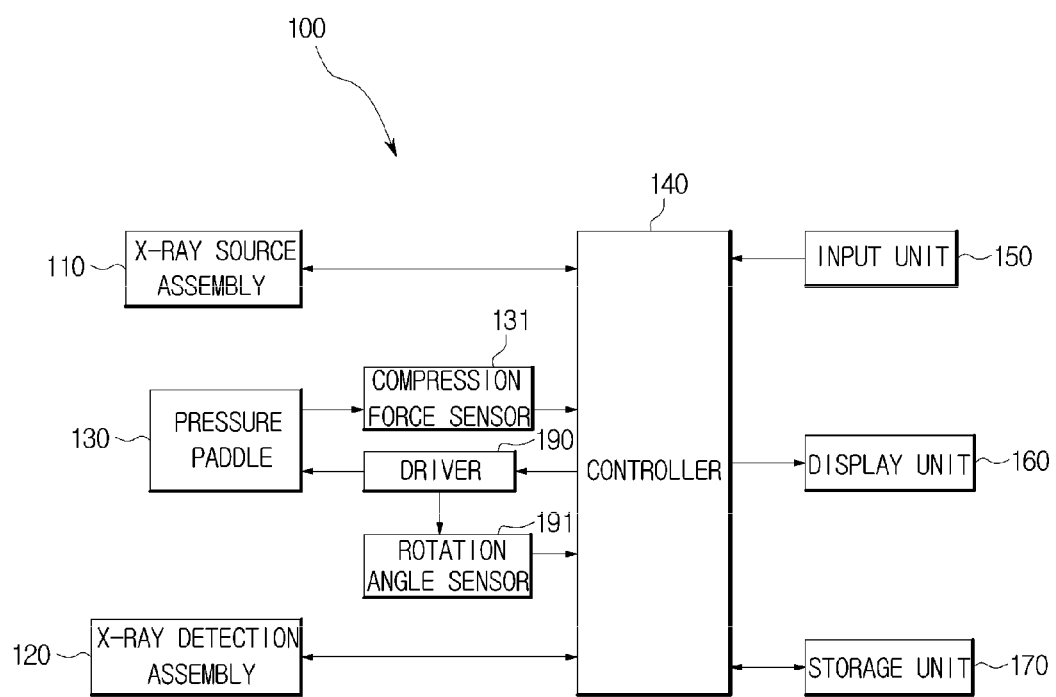
FIG. 5 is a block diagram illustrating a configuration of an X-ray imaging apparatus according to an exemplary embodiment of the present disclosure.

FIG. 5 is a block diagram illustrating a configuration of an X-ray imaging apparatus according to an exemplary embodiment of the present disclosure. As illustrated in FIG. 5, an X-ray imaging apparatus 100 may include the X-ray source assembly 110, the X-ray detection assembly 120, the pressure paddle 130, the compression force sensor 131, a controller 140, the input unit 150, a display unit 160, a storage unit 170, the driver 190, and the rotation angle sensor 191.

Because the pressure paddle 130, the compression force sensor 131, the driver 190, and the rotation angle sensor 191 have been described above with reference to FIGS. 1 to 4, repeated descriptions thereof will be omitted.

The X-ray source assembly 110 may include an X-ray tube 111 (see FIG. 6) to generate X-rays. The X-ray tube 111 will be described in more detail with reference to FIG. 6, below.

Figure 6:
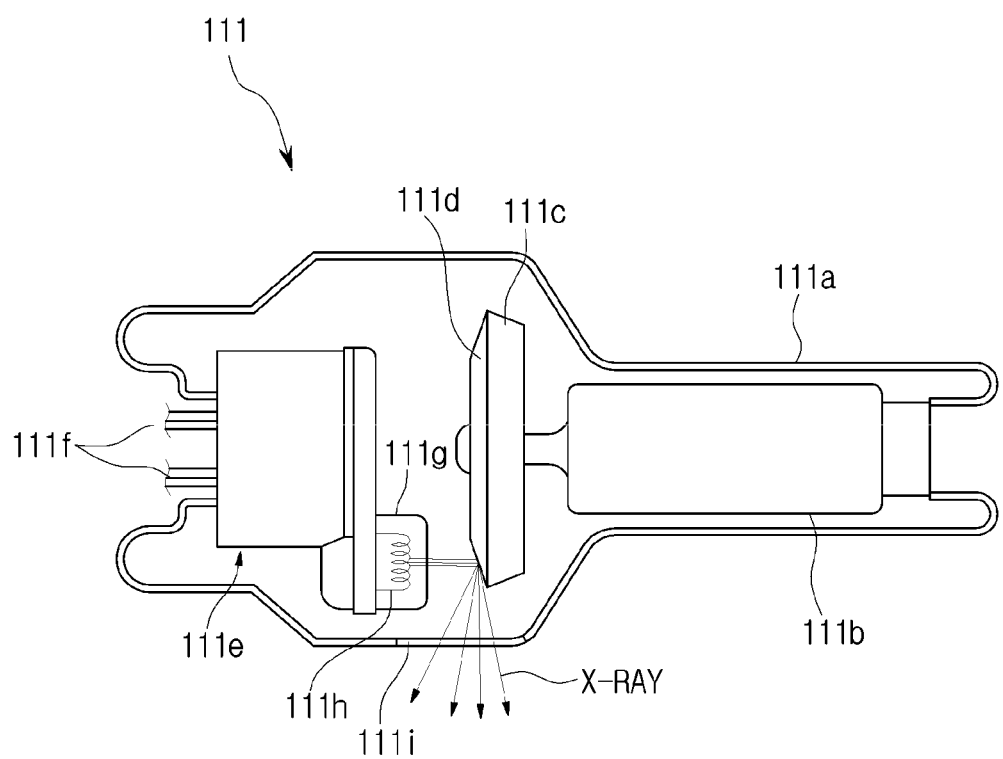
FIG. 6 illustrates an internal structure of an X-ray tube included in an X-ray source assembly according to an exemplary embodiment.

FIG. 6 illustrates an internal structure of the X-ray tube 111 included in the X-ray source assembly 110. Referring to FIG. 6, the X-ray tube 111 may be embodied as a two-electrode vacuum tube including an anode 111c and a cathode 111e. The body of the two-electrode vacuum tube may be a glass tube 111a made of silica (hard) glass or the like.

The cathode 111e includes a filament 111h and a focusing electrode 111g for focusing electrons, and the focusing electrode 111g is also called a focusing cup. The inside of a glass tube 111a is evacuated to a high vacuum state of about 10 mmHg, and the filament 111h of the cathode 111e is heated to a high temperature, thereby generating thermoelectrons. The filament 111h may be a tungsten filament, and the filament 111h may be heated by applying current to electrical leads 111f connected to the filament 111h. However, the cathode 111e may use, instead of the filament 111h, a carbon nano-tube that can be driven with high-speed pulses.

The anode 111c may be made of copper, and a target material 111d is applied on the surface of the anode 111c facing the cathode 111e, wherein the target material 111d may be a high-resistance material, e.g., Cr, Fe, Co, Ni, W, or Mo. The higher the melting point of the target material 111d, the smaller the focal spot size.

When a high voltage is applied between the cathode 111e and the anode 111c, thermoelectrons are accelerated and collide with the target material 111d of the anode 111e, thereby generating X-rays. The X-rays are irradiated toward the outside through a window 111i. The window 111i may be a Beryllium (Be) thin film. Also, a filter for filtering a specific energy band of X-rays may be provided on the front or rear side of the window 111i.

The target material 111d may be rotated by a rotor 111b. When the target material 111d rotates, the heat accumulation rate may increase 10 times per unit area and the focal spot size may be reduced, compared to when the target material 111d is fixed.

The voltage that is applied between the cathode 111e and the anode 111c of the X-ray tube 111 is called a tube voltage. The magnitude of a tube voltage may be expressed as a crest value (kVp).

When the tube voltage increases, velocity of thermoelectrons increases accordingly. Then, energy (energy of photons) of X-rays that are generated when the thermoelectrons collide with the target material 111d also increases. And, as the energy of X-rays increases, a larger amount of X-rays comes to be transmitted through the object 30. Accordingly, the X-ray detection assembly 120 (see FIG. 1) will detect a large amount of X-rays. As a result, an X-ray image having a high Signal-to-Noise Ratio (SNR), that is, an X-ray image having high quality can be obtained.

On the contrary, when the tube voltage decreases, velocity of thermoelectrons decreases accordingly. Then, energy (energy of photons) of X-rays that are generated when the thermoelectrons collide with the target material 111d also decreases. And, as the energy of X-rays decreases, a larger amount of X-rays comes to be absorbed or reflected in the target 30. Accordingly, the X-ray detection assembly 120 will detect a small amount of X-rays. As a result, an X-ray image having a low SNR, that is, an X-ray image having low quality will be obtained.

Current flowing through the X-ray tube 111 is called tube current, and can be expressed as an average value (mA). When tube current increases, a dose of X-rays (that is, X-ray photons) increases so that an X-ray image having a high SNR is obtained. On the contrary, when tube current decreases, a dose of X-rays decreases so that an X-ray image having a low SNR is obtained.

In summary, energy of X-rays can be controlled by adjusting a tube voltage. Also, a dose or intensity of X-rays can be controlled by adjusting tube current and an X-ray exposure time. In other words, by controlling a tube voltage or tube current according to the kind or properties of an object, an energy or dose of X-rays to be irradiated can be controlled.

X-rays that are irradiated from the X-ray tube 111 have a specific energy band that is defined by upper and lower limits. The upper limit of the specific energy band, that is, maximum energy of X-rays to be irradiated may be adjusted by the magnitude of a tube voltage. The lower limit of the specific energy band, that is, minimum energy of X-rays to be irradiated may be adjusted by a filter aligned in a direction in which X-rays are irradiated. Specifically, by filtering out X-rays having a low energy band using the filter, average energy of X-rays to be irradiated can be increased. Energy of X-rays to be irradiated may be expressed as maximum energy or average energy.

Figure 7:
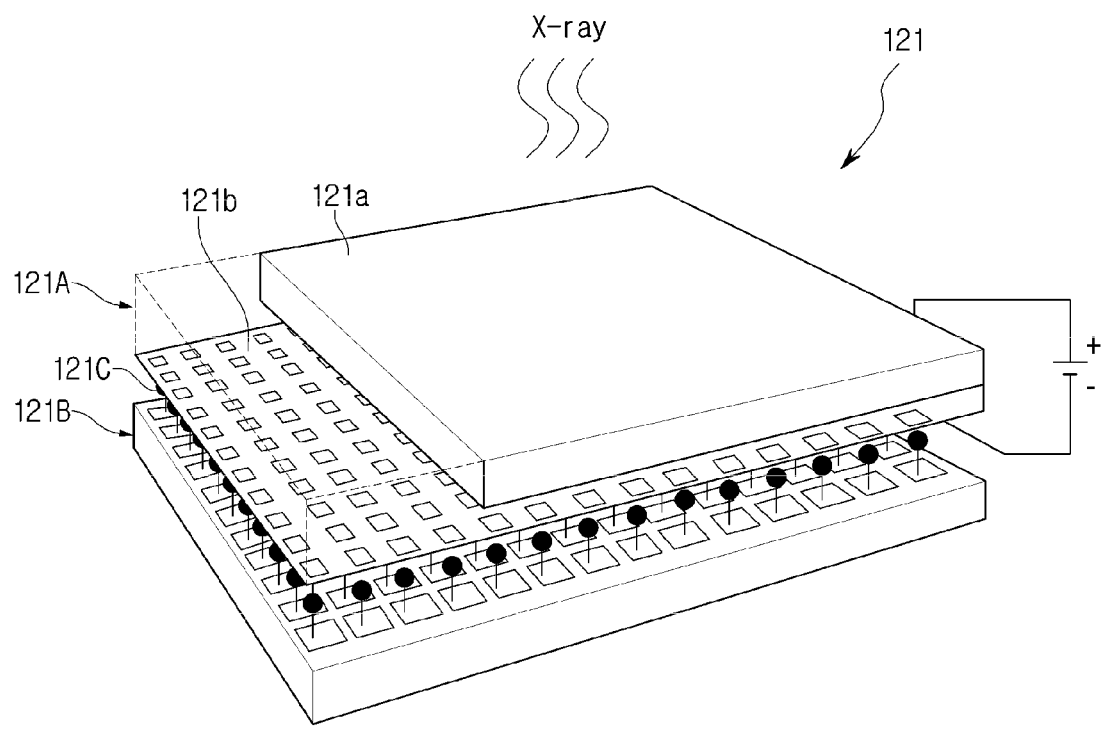
FIG. 7 illustrates a structure of an X-ray detector included in an X-ray detection assembly according to an exemplary embodiment.

Referring again to FIG. 5, the X-ray detection assembly 120 may include an X-ray detector 121 (see FIG. 7). The X-ray detector 121 may detect X-rays transmitted through the object 30, and convert the X-rays into electrical signals. The X-ray detector 121 will be described in more detail with reference to FIG. 7, below.

FIG. 7 illustrates a structure of the X-ray detector 121 included in the X-ray detection assembly 120 according to an exemplary embodiment.

Referring to FIG. 7, the X-ray detector 121 may include a light receiving device 121A to detect X-rays and convert the X-rays into electrical signals, and a read circuit 121B to read out the electrical signals. The read circuit 121B may be in the form of a 2D pixel array including a plurality of pixel areas. The light receiving device 121A may be made of a single crystal semiconductor material in order to ensure high resolution, high response speed, and a high dynamic area even under conditions of low energy and a small dose of X-rays. The single crystal semiconductor material may be Ge, CdTe, CdZnTe, or GaAs.

The light receiving device 121A may be in the form of a PIN photodiode. The PIN photodiode is fabricated by bonding a p-type layer 121b in which p-type semiconductors are arranged in the form of a 2D pixel array on the lower surface of a n-type semiconductor substrate 121a having high resistance. The read circuit 121B, which is fabricated according to a Complementary Metal Oxide Semiconductor (CMOS) process, is coupled with the light receiving device 121A in units of pixels. The CMOS read circuit 121B and the light receiving device 121A may be coupled by a Flip-Chip Bonding (FCB) method. More specifically, the CMOS read circuit 121B and the light receiving device 121A may be coupled by forming bumps 121C with PbSn, In, or the like, reflowing, applying heat, and then compressing. However, the X-ray detector 121 is not limited to this structure.

Referring again to FIG. 5, the storage unit 170 may store data and algorithms required for operations of the X-ray imaging apparatus 100, and also store data or X-ray images generated while the X-ray imaging apparatus 100 operates. The storage unit 170 may be embodied as a volatile memory device, a non-volatile memory device, a hard disk, an optical disk, or a combination thereof. However, the storage unit 170 is not limited to the above-mentioned devices, and may be embodied as any storage device well-known in the art.

The input unit 150 may receive instructions or commands for controlling operations of the X-ray imaging apparatus 100. To do this, the input unit 150 may be embodied as a keyboard, a mouse, a touch pad, a piezoelectric/gyroscopic sensor, a camera sensor, a microphone, or a combination thereof.

The display unit 160 may be separate from the input unit 150 or integrated with the input unit 150. The display unit 160 may display an X-ray image of a breast. Also, the display unit 160 may display information about radiography conditions for X-ray images, or information about a breast. The information about the radiography conditions for X-ray images may include information about an X-ray source, information about a tube voltage, information about tube current, and information about a filter. The information about the X-ray source may be a kind of a target material. The information about the breast may include information about a thickness of the pressed breast, information about a size of the pressed breast, and information about breast density.

Breast density represents a ratio of fibroglandular tissue with respect to entire materials constituting the breast. In detail, if a breast is composed of adipose tissue and fibroglandular tissue, when the breast contains more fibroglandular tissue than adipose tissue, the breast can be determined to have high breast density, whereas when the breast contains more adipose tissue than fibroglandular tissue, the breast can be determined to have low breast density. Breast density can be generally classified into four levels. A case in which a ratio of fibroglandular tissue with respect to entire materials constituting a breast is 25% or less may be classified into a first level, a case in which a ratio of fibroglandular tissue with respect to entire materials constituting a breast is from 26% to 50% may be classified into a second level, a case in which a ratio of fibroglandular tissue with respect to entire materials constituting a breast is from 51% to 75% may be classified into a third level, and a case in which a ratio of fibroglandular tissue with respect to entire materials constituting a breast is from 76% to 100% may be classified into a fourth level.

The fibroglandular tissue of the breast is shown brightly in an X-ray image, whereas the adipose tissue of the breast is shown darkly in an X-ray image. If breast density corresponds to the first level or the second level, it is possible to easily distinguish breast tumors that exist in the breast from an X-ray image. However, if breast density corresponds to the third level or the fourth level, it is difficult to distinguish breast tumors from fibroglandular tissue in an X-ray image although the breast tumors exist in the breast. Accordingly, a patient having high breast density may also undergo breast ultrasonography in addition to an X-ray examination.

Thus, breast density may be considered to be important information about the breast. According to a typical method of calculating breast density, if an operator selects a breast area and/or a fibroglandular tissue area having a brightness value that is equal to or greater than a predetermined value in an X-ray image, breast density is calculated by dividing a size of the fibroglandular tissue area by a size of the breast area. However, in the typical method, because the operator selects a breast area and/or a fibroglandular tissue area, the calculated breast density will be a subjective value.

However, according to the present disclosure, volumes of a breast may be reconstructed from an X-ray image for the breast where it is assumed that the breast consists of only adipose tissue, an X-ray image for the breast where it is assumed that the breast consists of only fibroglandular tissue, and an X-ray image obtained by irradiating X-rays toward the pressed breast, and then, breast density is calculated based on the reconstructed volumes. As such, if breast density is calculated based on the volumes reconstructed from the respective X-ray images, more accurate breast density can be obtained than when breast density is calculated based on areas in an X-ray image. The breast density may be calculated by the controller 140.

The controller 140 may produce an X-ray image for the pressed breast based on electrical signals output from the individual pixels of the X-ray detection assembly 120. Also, the controller 140 may produce an X-ray image for the pressed breast when it is assumed that the pressed breast consists of only adipose tissue, and an X-ray image for the pressed breast when it is assumed that the pressed breast consists of only fibroglandular tissue. Hereinafter, for convenience of description, an X-ray image for the pressed breast when it is assumed that the pressed breast consists of only adipose tissue is referred to as a "first reference image", and an X-ray image for the pressed breast when it is assumed that the pressed breast consists of only fibroglandular tissue is referred to as a "second reference image".

Figure 8:
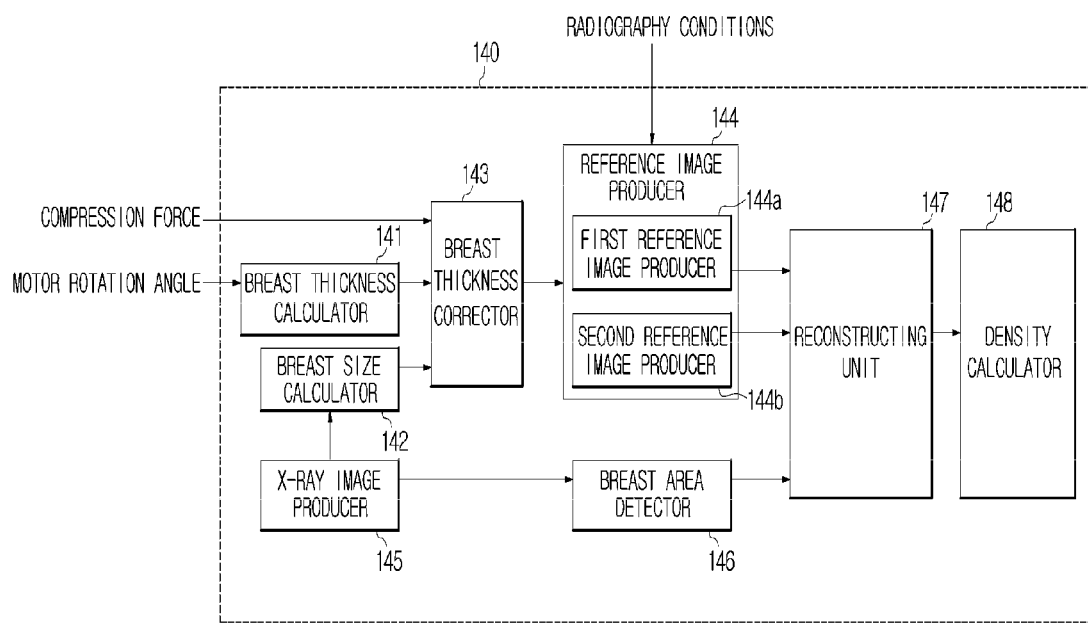
FIG. 8 is a block diagram illustrating a configuration of a controller, similar to that shown in FIG. 5, according to an exemplary embodiment.

FIG. 8 is a block diagram illustrating a configuration of the controller 140. Referring to FIG. 8, the controller 140 may include a breast thickness calculator 141, a breast size calculator 142, a breast thickness corrector 143, a reference image producer 144, an X-ray image producer 145, a breast area detector 146, a reconstructing unit 147, and a density calculator 148.

The X-ray image producer 145 may produce an X-ray image based on electrical signals output from the individual pixels of the X-ray detector 121. The produced X-ray image may be provided to the breast size calculator 142 and the breast area detector 146, which will be described later.

The breast area detector 146 may pre-process the X-ray image, and detect a breast area which is an area occupied by the pressed breast from the pre-processed X-ray image. Pre-processing an X-ray image may be done to eliminate artifacts or noise that exists in the X-ray image. Thereafter, the breast area detector 146 may detect a boundary line of the breast from the pre-processed X-ray image to thereby detect a breast area. Information about the detected breast area may be provided to the reconstructing unit 147.

Figure 9:
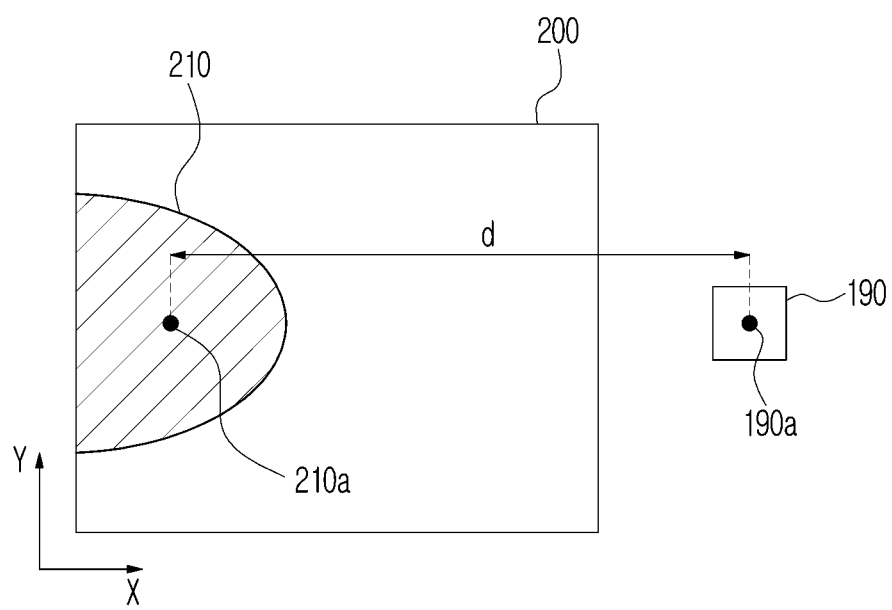
FIG. 9 is a view for describing a method of calculating size information of a breast based on an X-ray image according to an exemplary embodiment.

The breast size calculator 142 may analyze the X-ray image produced by the X-ray image producer 145 to calculate a size of the breast. As shown in FIG. 9, the breast size calculator 142 may detect a breast area 210 from an X-ray image 200, and detect a center point 210a of the detected breast area 210. Then, the breast size calculator 142 may calculate a distance d between the detected center point 210a of the breast area 210 and a center point 190a of the driver 190. Thereafter, the breast size calculator 142 may calculate a size of the breast based on the calculated distance d.

Generally, as the size of a pressed breast is greater, the center point 210a of the breast area 210 is closer to the center point 190a of the driver 190, and as the size of a pressed breast is smaller, the center point 210a of the breast area 210 is further from the center point 190a of the driver 190. As such, because the distance d between the center point 210a of the breast area 210 and the center point 190a of the driver 190 is inverse-proportional to a size of the breast, a size of the breast can be calculated by measuring a distance d between the center point 210a of the breast area 210 and the center point 190a of the driver 190. Information about the calculated size of the breast may be provided to the breast thickness corrector 143.

Referring again to FIG. 8, the breast thickness calculator 141 may calculate a thickness of the pressed breast, based on information about a rotation angle of the motor detected by the rotation angle sensor 191. More specifically, the breast thickness calculator 141 may calculate a movement distance of the pressure paddle 130 from detected rotation angle information, and then subtract the movement distance of the pressure paddle 130 from a distance between the breast contact unit 123 and the pressure paddle 130 before the pressure paddle 130 is moved, thereby obtaining thickness information of the pressed breast. The thickness information of the pressed breast may be provided to the breast thickness corrector 143.

The breast thickness corrector 143 may correct the thickness information of the breast calculated by the breast thickness calculator 141, based on information about a compression force applied to the breast and the breast size information calculated by the breast size calculator 142. Specifically, because the thickness information of the breast calculated by the breast thickness calculator 141 corresponds to the thickness of a breast part placed close to the driver 190, the breast thickness corrector 143 may correct the thickness information of the breast calculated by the breast thickness calculator 141 such that it approximates thickness information of the real breast. The corrected thickness information of the breast may be provided to the reference image producer 144.

The reference image producer 144 may include a first reference image producer 144a to produce a first reference image, and a second reference image producer 144b to produce a second reference image.

As described above, the first reference image is an X-ray image that is obtained when a pressed breast consists of only adipose tissue, and the second reference image is an X-ray image that is obtained when a pressed breast consists of only fibroglandular tissue.

The first reference image producer 144a and the second reference image producer 144b may produce the first reference image and the second reference image, respectively, using Equation (1), below.

$$I=I_0 e^{-\mu t} \quad (1)$$

In Equation (1), $I_0$ represents intensity of X-rays that are irradiated by the X-ray tube 111. The intensity of X-rays that are irradiated by the X-ray tube 111 may be obtained from information about radiography conditions. The information about radiography conditions may include information about an X-ray source, information about a tube voltage, information about tube current, and information about a filter. In Equation (1), $\mu$ represents an attenuation coefficient of tissue. As described above, because different materials constituting a breast have different attenuation coefficients, attenuation coefficients of materials may be stored in the storage unit 170. t represents a thickness of the pressed breast.

The first reference image is, as described above, an X-ray image of a pressed breast when it is assumed that the pressed breast consists of only adipose tissue. Accordingly, the first reference image producer 144a may use an attenuation coefficient for adipose tissue of a breast as the $\mu$ value to produce the first reference image according to Equation (1). The first reference image may be provided to the reconstructing unit 147 which will be described later.

Because the second reference image is, as described above, an X-ray image of a pressed breast when it is assumed that the pressed breast consists of only fibroglandular tissue, the second reference image producer 144b may use an attenuation coefficient for fibroglandular tissue of a breast as the $\mu$ value to produce the second reference image according to Equation (1). The second reference image may be provided to the reconstructing unit 147.

The reconstructing unit 147 may reconstruct volumes of the pressed breast from the first reference image, the second reference image, and the X-ray image. Reconstructing a volume of a pressed breast from an image may include representing X-ray intensities of the individual pixels of the corresponding image in a 3-Dimensional (3D) space.

Figure 10A:
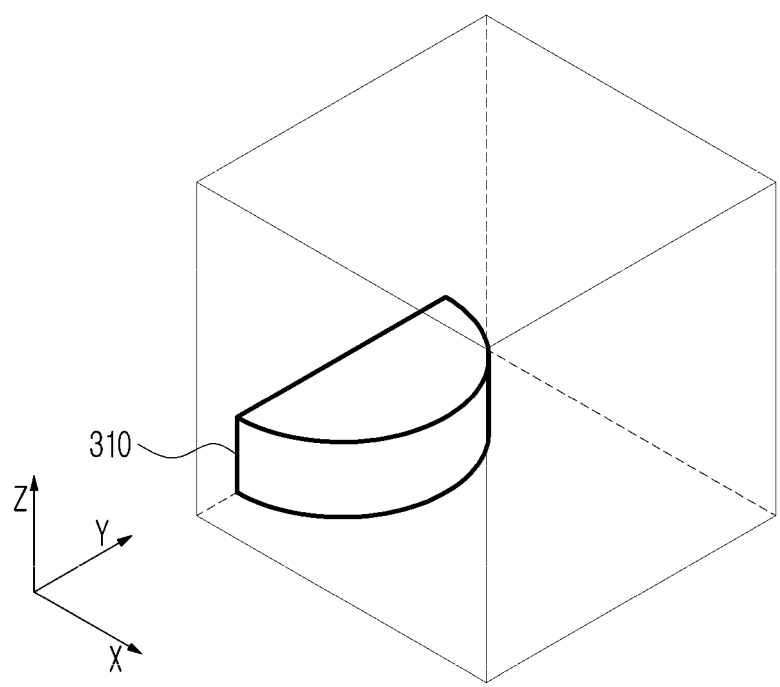
FIG. 10A shows an image obtained by reconstructing a volume of a pressed breast from a first reference image according to an exemplary embodiment.

FIG. 10A shows an image obtained by reconstructing a volume of the pressed breast from the first reference image. Because the first reference image is an X-ray image for the pressed breast when it is assumed that the pressed breast consists of only adipose tissue, intensities of the individual pixels in the first reference image have generally low values. Accordingly, when a volume 310 of the pressed breast is reconstructed from the first reference image, a height of the reconstructed volume 310 is also low.

Figure 10B:
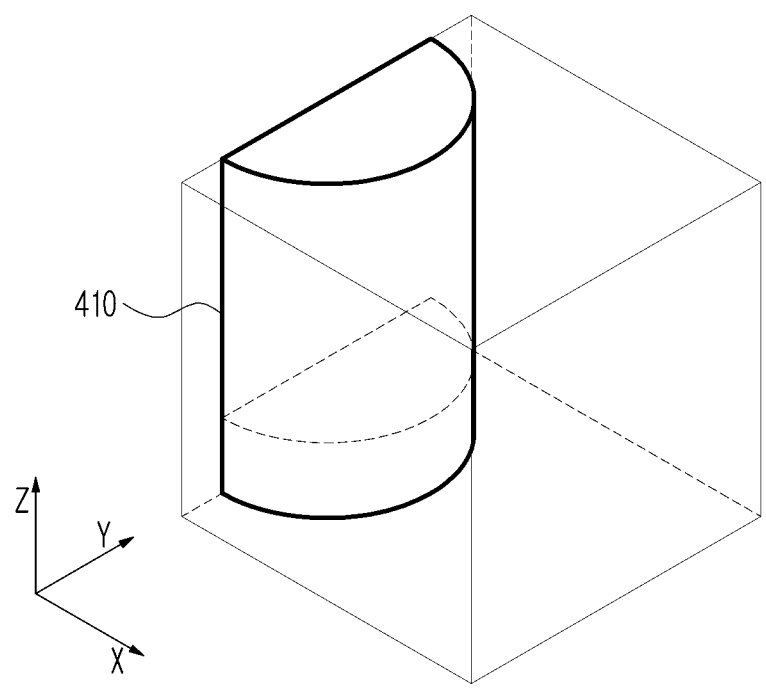
FIG. 10B shows an image obtained by reconstructing a volume of a pressed breast from a second reference image according to an exemplary embodiment.

FIG. 10B shows an image obtained by reconstructing a volume of the pressed breast from the second reference image. Because the second reference image is an X-ray image for the pressed breast when it is assumed that the pressed breast consists of only fibroglandular tissue, intensities of the individual pixels in the second reference image have generally high values. Accordingly, when a volume 410 of the pressed breast is reconstructed from the first reference image, a height of the reconstructed volume 410 is also high.

Figure 10C:
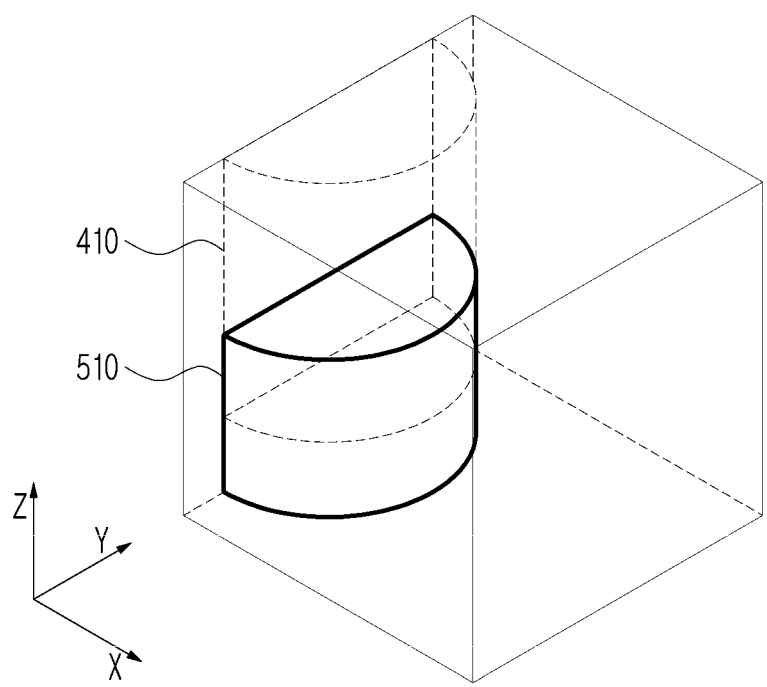
FIG. 10C shows an image obtained by reconstructing a volume of a pressed breast from an X-ray image according to an exemplary embodiment.

FIG. 10C shows an image obtained by reconstructing a volume of the pressed breast from the X-ray image. Because the X-ray image (200 of FIG. 9) is an image obtained by irradiating X-rays toward a breast consisting of adipose tissue and fibroglandular tissue, intensities of the individual pixels in the X-ray image 200 have values between the intensity values of the first reference image and the intensity values of the second reference image. Accordingly, when a volume 510 of the pressed breast is reconstructed from the X-ray image 200, a height of the reconstructed volume 510 will be between the height of the volume 310 reconstructed from the first reference image and the height of the volume 410 reconstructed from the second reference image.

In FIGS. 10A to 10C, for convenience of description, each reconstructed volume is shown in the form of a cylinder whose upper side is a semicircle shape. However, in the first reference image, the second reference image, and the X-ray image, the intensities of the individual pixels in the breast area may have different values. Accordingly, in FIGS. 10A, 10B, and 10C, the upper side of each cylinder may be shown as a curved shape.

Figure 10D:
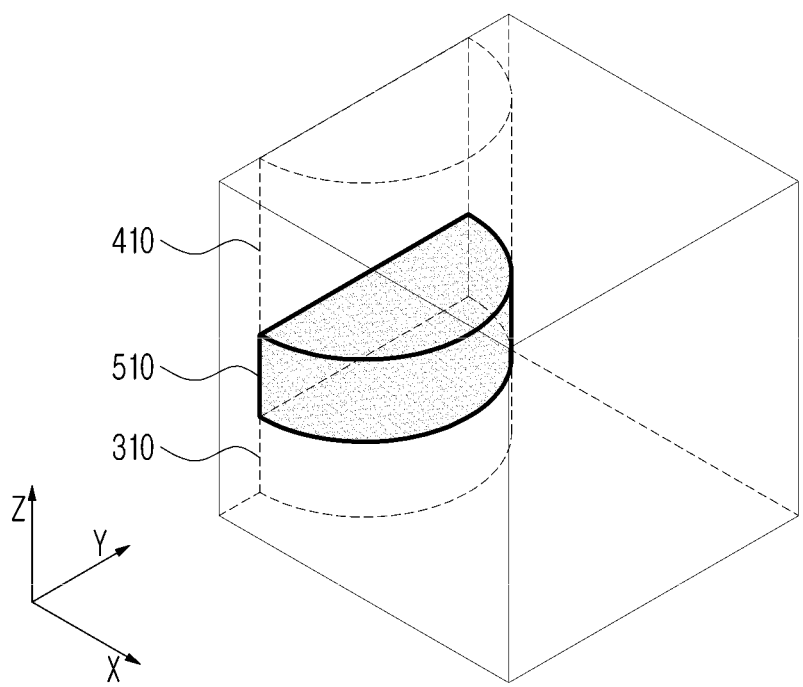
FIG. 10D shows breast density calculated from volumes shown in FIGS. 10A, 10B, and 10C according to an exemplary embodiment.

As shown in FIGS. 10A, 10B, and 10C, after the volumes of the pressed breast are reconstructed from the first reference image, the second reference image, and the X-ray image, as shown in FIG. 10D, a difference between the volume 510 of the pressed breast reconstructed from the X-ray image and the volume 310 of the pressed breast reconstructed from the first reference image may be calculated. That is, the volume of the breast consisting of only adipose tissue is subtracted from the volume of the breast consisting of adipose tissue and fibroglandular tissue. As a result, the volume of fibroglandular tissue among the entire materials of the breast remains, and the volume of fibroglandular tissue can be understood to be breast density.

Referring again to FIG. 8, the density calculator 148 may calculate, as described above with reference to FIG. 10D, density of the breast, based on the volumes of the breast reconstructed respectively from the first reference image, the second reference image, and the X-ray image.

According to an exemplary embodiment, information about the calculated density of the breast may be displayed through the display 160. According to another exemplary embodiment, information about the calculated density of the breast may be added as tag information of the X-ray image 200. If the information about the breast density is added as tag information of the X-ray image 200, the X-ray image 200 may be classified according to the information about the breast density.

Figure 11:
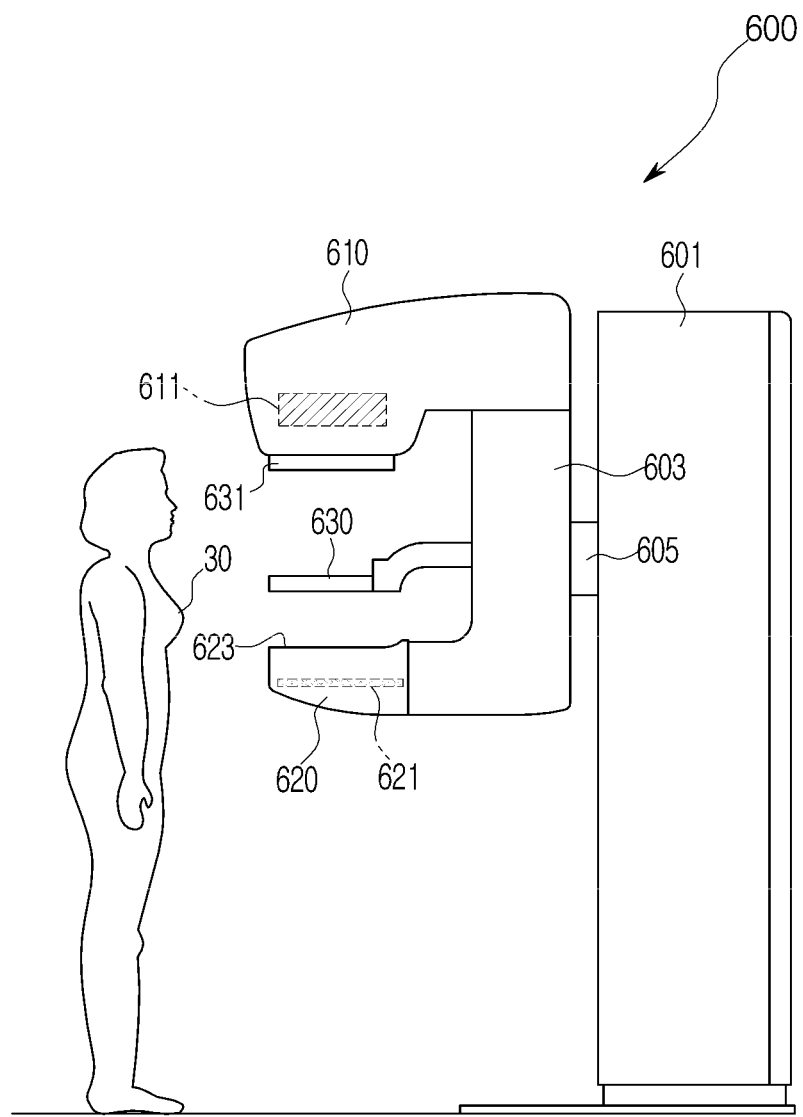
FIG. 11 illustrates an external appearance of an X-ray imaging apparatus according to another exemplary embodiment of the present disclosure.

FIG. 11 illustrates an external appearance of an X-ray imaging apparatus according to another exemplary embodiment of the present disclosure. Referring to FIG. 11, an X-ray imaging apparatus 600 may include a main body 601, a frame 603, an arm 605, an X-ray source assembly 610 including an X-ray tube 611, an X-ray detection assembly 620 including an X-ray detector 621 and a breast contact part 623, a pressure paddle 630, and a distance sensor array 631.

The main body 601, the frame 603, the arm 605, the X-ray source assembly 610, the X-ray detection assembly 620, and the pressure paddle 630 among the aforementioned components are the same components as the main body 101, the frame 103, the arm 105, the X-ray source assembly 110, the X-ray detection assembly 120, and the pressure paddle 130, as described above with reference to FIG. 1.

The distance sensor array 631 may be configured by arranging a plurality of distance sensors two-dimensionally, and fixed on the lower portion of the X-ray source assembly 610. If a breast placed on the breast contact part 623 is pressed by the pressure paddle 630, the distance sensor array 631 may detect a distance to the pressure paddle 630. Thickness information of the breast can be obtained by the distance information detected by the distance sensor array 631.

Figure 12:
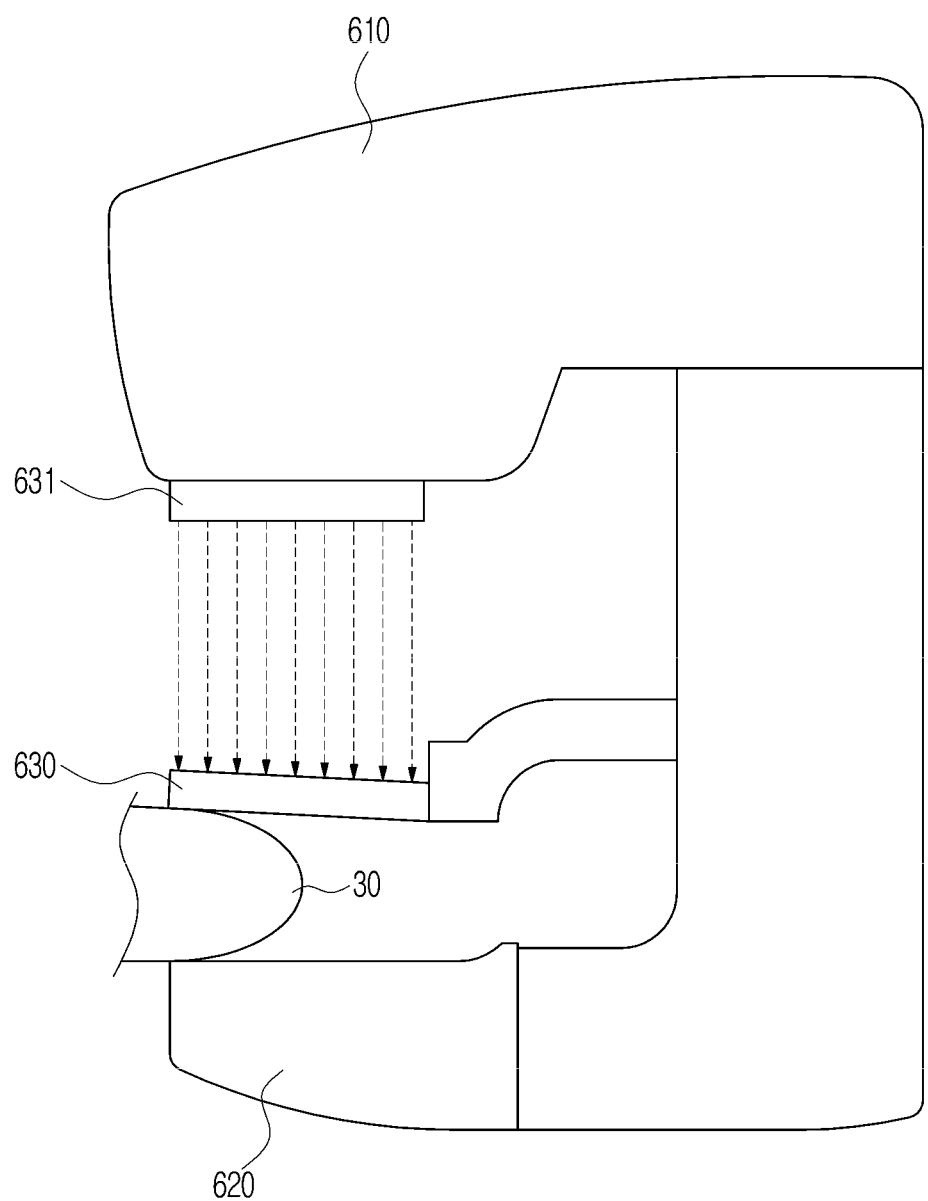
FIG. 12 is a view for illustrating a method of acquiring thickness information of a breast in an X-ray imaging apparatus, similar to that shown in FIG. 11, according to an exemplary embodiment.

FIG. 12 is a view for describing a method of obtaining thickness information of a breast in the X-ray imaging apparatus 600 illustrated in FIG. 11.

Although not shown in FIG. 12, the distance sensor array 631 may include an infrared irradiator to irradiate infrared rays toward the pressure paddle 630, and an infrared receiver to receive infrared rays reflected from the pressure paddle 630.

For example, the distance sensor array 631 may irradiate, as shown in FIG. 12, infrared rays toward the pressure paddle 630, and then detect a distance to the pressure paddle 630 based on a time taken until the infrared rays are received by the infrared receiver.

According to another exemplary embodiment, the distance sensor array 631 may irradiate infrared rays toward the pressure paddle 630, and then detect a distance to the pressure paddle 630 based on intensity of infrared rays reflected from the pressure paddle 630 and then received by the infrared receiver.

Figure 13:
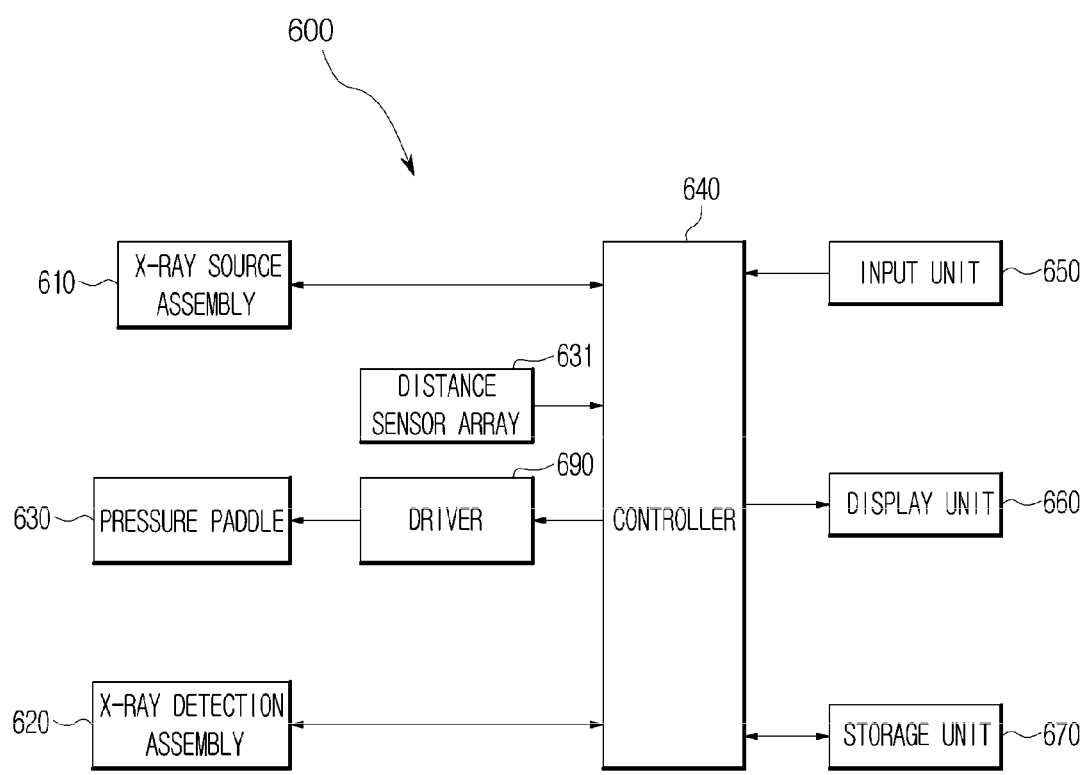
FIG. 13 is a block diagram illustrating a configuration of an X-ray imaging apparatus according to another exemplary embodiment of the present disclosure.

FIG. 13 is a block diagram illustrating a configuration of an X-ray imaging apparatus according to another exemplary embodiment of the present disclosure. As shown in FIG. 13, an X-ray imaging apparatus 600 may include an X-ray source assembly 610, an X-ray detection assembly 620, a pressure paddle 630, a distance sensor array 631, a controller 640, an input unit 650, a display unit 660, a storage unit 670, and a driver 690.

The X-ray source assembly 610, the X-ray detection assembly 620, the pressure paddle 630, the input unit 650, the display unit 660, the storage unit 670, and the driver 690, except for the distance sensor array 631 and the controller 640, among the components shown in FIG. 13 are similar to or the same as the X-ray source assembly 110, the X-ray detection assembly 120, the pressure paddle 130, the input unit 150, the display unit 160, the storage unit 170, and the driver 190 as described above with reference to FIG. 5, and accordingly, repeated descriptions thereof will be omitted.

The distance sensor array 631 may be, as described above, configured by arranging a plurality of distance sensors two-dimensionally, and detect information about a distance to the pressure paddle 630. Information about the distance detected by the distance sensor array 631 may be provided to the controller 640.

The controller 640 may produce an X-ray image based on electrical signals output from the individual pixels of the X-ray detector 121. Also, the controller 640 may interpolate distance information detected by the distance sensor array 631, and calculate a thickness of a breast based on the interpolated distance information. Also, the controller 640 may produce a first reference image and a second reference image, based on thickness information of a pressed breast and information about radiography conditions for X-ray images, and calculate density of the breast based on volumes of the pressed breast reconstructed from the first reference image, the second reference image, and the X-ray image.

Figure 14:
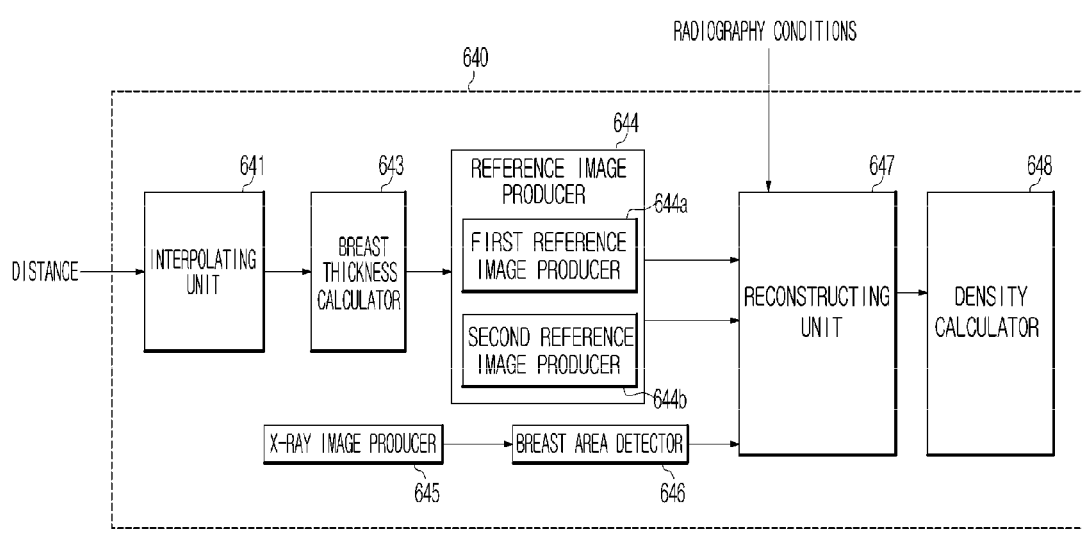
FIG. 14 is a block diagram illustrating a configuration of a controller, similar to that shown in FIG. 13, according to an exemplary embodiment.

Hereinafter, a configuration and operations of the controller 640 will be described in more detail with reference to FIG. 14. FIG. 14 is a block diagram illustrating a configuration of the controller 640. Referring to FIG. 14, the controller 640 may include an interpolator 641, a breast thickness calculator 643, a reference image producer 644, an X-ray image producer 645, a breast area detector 646, a reconstructing unit 647, and a density calculator 648.

Unlike the controller 140 illustrated in FIG. 8, the controller 640 illustrated in FIG. 14 may further include the interpolator 641 and the breast thickness calculator 643.

The interpolator 641 may interpolate distance information detected by the distance sensor array 631. In detail, the distance sensor array 631 may include a plurality of distance sensors arranged two-dimensionally, and the distance sensors may be spaced at regular intervals. Accordingly, there may be an area for which distance information cannot be detected. The interpolator 641 may interpolate distance information acquired by two neighboring distance sensors to acquire distance information of an area for which no distance sensor is disposed. By performing interpolation with respect to all the distance sensors, distance information for the entire area of the pressure paddle 630 may be acquired. The distance information interpolated by the interpolator 641 may be provided to the breast thickness calculator 643.

The breast thickness calculator 643 may calculate thickness information of the pressed breast, based on the interpolated distance information. Referring to FIGS. 11 to 13, by subtracting a distance from the distance sensor array 631 to the pressure paddle 630 and the thickness of the pressure paddle 630 from a distance from the distance sensor array 631 to the breast contact part 623, thickness information of the pressed breast may be acquired. The distance from the distance sensor array 631 to the breast contact part 623 and the thickness of the pressure paddle 630 may have been stored in advance in the storage unit 670. The thickness information of the breast calculated by the breast thickness calculator 643 may be provided to the reference image producer 644.

FIG. 15 is a flowchart illustrating a control method of an X-ray imaging apparatus, according to an exemplary embodiment of the present disclosure.

Referring to FIGS. 1 and 15, an operator may place a breast that is a subject, on the breast contact part 123. Then, the operator may move the pressure paddle 130 downward to press the breast (S810). The pressure paddle 130 may be moved manually or automatically. Specifically, the operator may hold a handle provided around the pressure paddle 130 to move the pressure paddle 130 downward, or may manipulate the input unit 150 to move the pressure paddle 130 downward.

After the breast is pressed by the pressure paddle 130, thickness information of the pressed breast may be acquired (S820). The thickness information of the pressed breast may be acquired in various methods. For example, as shown in FIG. 2, if the driver 190 connected to the pressure paddle 130 is a motor, and the pressure paddle 130 is moved in an up-down direction by rotation of the motor, a rotation angle of the motor may be detected using the rotation angle sensor 191, and thickness information of the pressed breast may be acquired based on the detected rotation angle. As another example, as shown in FIG. 12, if the distance sensor array 631 is fixed on the lower part of the X-ray source assembly 110, thickness information of the pressed breast may be acquired based on distance information acquired by the distance sensor array 631.

Thereafter, radiography conditions required for X-ray scanning may be set and X-rays may be irradiated (S830). If the operator manipulates the input unit 150 to set radiography conditions for X-ray scanning, the X-ray tube 111 of the X-ray source assembly 110 may generate X-rays, and the generated X-rays may be irradiated to the pressed breast.

Then, an X-ray image may be acquired based on electrical signals output from the individual pixels of the X-ray detector 121 (S840). The acquired X-ray image may be used to calculate size information of the breast and to calculate breast density.

Successively, a first reference image and a second reference image may be produced based on the thickness information of the pressed breast and information about the radiography conditions (S850). The first reference image may be an X-ray image for the pressed breast when it is assumed that the pressed breast consists of only adipose tissue. The second reference image may be an X-ray image for the pressed breast when it is assumed that the pressed breast consists of only fibroglandular tissue. The first reference image and the second reference image may be produced according to Equation (1), as described above. More specifically, the first reference image may be produced using the information about the radiography conditions, the thickness information of the pressed breast, and an X-ray attenuation coefficient for the adipose tissue of the breast, and the second reference image may be produced using the information about the radiography conditions, the thickness information of the pressed breast, and an X-ray attenuation coefficient for the fibroglandular tissue of the breast.

Thereafter, volumes of the pressed breast may be reconstructed from the first reference image, the second reference image, and the X-ray image, respectively (S860). A volume 310 of the pressed breast reconstructed from the first reference image is shown in FIG. 10A, a volume 410 of the pressed breast reconstructed from the second reference image is shown in FIG. 10B, and a volume 510 of the pressed breast reconstructed from the X-ray image is shown in FIG. 10C.

After the volumes 310, 410, and 510 of the pressed breast are reconstructed from the first reference image, the second reference image, and the X-ray image, respectively, density of the breast may be calculated based on the volumes 310, 410, and 510 (S870). Specifically, a difference between the volume 510 of the pressed breast reconstructed from the X-ray image and the volume 310 of the pressed breast reconstructed from the first reference image may be calculated as a volume. The calculated volume, which represents the proportion of the different tissues that make up the breast, can be understood to be the density of the breast.

Additionally, according to another exemplary embodiment, during operation S840, information about the density of the breast may be displayed through the display unit 160. As another example, information about the density of the breast may be added to tag information of the X-ray image 200 together with the information about the radiography conditions.

Therefore, according to the exemplary embodiments of the present disclosure as described above, it is possible to provide information about accurate breast density, rather than when breast density is calculated based on a ratio of an area having intensity values greater than a predetermined value with respect to the entire breast area of an X-ray image.

Because accurate breast density may be provided, it may be possible to improve the reliability of diagnosis based on X-ray images.

Exemplary embodiments of the present disclosure have been described above. In the exemplary embodiments described above, some of components constituting the X-ray imaging apparatus 100 may be implemented as a "module". Here, the term 'module' means, but is not limited to, a software and/or hardware component, such as a Field Programmable Gate Array (FPGA) or Application Specific Integrated Circuit (ASIC), which performs certain tasks. A module may advantageously be configured to reside on the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

With that being said, and in addition to the above described exemplary embodiments, exemplary embodiments of the present disclosure can thus be implemented through computer readable code/instructions in/on a medium, e.g., a computer readable medium, to control at least one processing element to implement any above described exemplary embodiment. The medium can correspond to any medium/media permitting the storing and/or transmission of the computer readable code.

The computer-readable code can be recorded on a medium or transmitted through the Internet. The medium may include Read Only Memory (ROM), Random Access Memory (RAM), Compact Disk-Read Only Memories (CD-ROMs), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

Although a few exemplary embodiments of the present disclosure have been shown and described, it would be appreciated by those skilled in the art that changes may be made in these exemplary embodiments without departing from the principles and spirit of the disclosure, the scope of which is defined in the claims and their equivalents.

What is claimed is:

1. An X-ray imaging apparatus comprising:
    a reconstructing unit configured to reconstruct a plurality of volumes relating to an object, the plurality of volumes related to the object comprising:
        a first volume being generated based on an object area as a base and intensities of pixels in an X-ray image of the object as a first height;
        a second volume being generated based on the object area as the base and intensities of pixels in a first reference image of the object as a second height, the first reference image being generated based on the object being of only adipose tissue; and
        a third volume being generated based on the object area as the base and intensities of pixels in a second reference image of the object as a third height, the second reference image being generated based on the object being of only fibroglandular tissue; and
    a density calculator configured to calculate a density of the object that is a ratio of fibroglandular tissue of the object with respect to entire tissue of the object using the reconstructed first, second and third volumes,
    wherein the density calculator is further configured to calculate the density based on a difference between the first volume of the object reconstructed from the X-ray image and the second volume of the object reconstructed from the first reference image.

2. The X-ray imaging apparatus of claim 1, further comprising:
    a pressure paddle disposed between an X-ray source assembly and an X-ray detection assembly and configured to press the object;
    a first reference image producer configured to produce the first reference image based on thickness information of the pressed object and an X-ray attenuation coefficient of adipose tissue; and
    a second reference image producer configured to produce the second reference image based on the thickness information of the pressed object and an X-ray attenuation coefficient of fibroglandular tissue.

3. The X-ray imaging apparatus of claim 2, further comprising:
    a driver configured to move the pressure paddle in an up direction and down direction;
    a rotation angle sensor configured to detect a rotation angle of the driver; and
    a thickness calculator configured to calculate the thickness information of the pressed object based on the rotation angle detected by the rotation angle sensor.

4. The X-ray imaging apparatus of claim 3, further comprising a thickness corrector configured to correct the thickness information calculated by the thickness calculator, based on a size of the object and a compression force applied to the object.

5. The X-ray imaging apparatus of claim 4, further comprising a size calculator configured to calculate the size of the object based on a distance between a center point of an object area detected from the X-ray image, and a center point of the driver.

6. The X-ray imaging apparatus of claim 4, further comprising a compression force sensor disposed on a lower surface of the pressure paddle, and configured to detect the compression force applied to the object.

7. The X-ray imaging apparatus of claim 2, further comprising:
    a distance sensor array disposed in a lower portion of the X-ray source assembly, and configured to detect a distance to the pressure paddle; and
    a thickness calculator configured to calculate the thickness information of the pressed object based on the distance detected by the distance sensor array.

8. The X-ray imaging apparatus of claim 7, further comprising an interpolator configured to interpolate the distance detected by the distance sensor array.

9. The X-ray imaging apparatus of claim 2, wherein the reconstructing unit is further configured to reconstruct the first, second and third volumes relating to the object from the X-ray image, the first reference image, and the second reference image, respectively, based on the thickness information of the pressed object and information about radiography conditions of the X-ray image.

10. The X-ray imaging apparatus of claim 9, wherein the information about the radiography conditions includes at least one of information about a tube voltage, information about tube current, information about a filter, and information about an X-ray source.

11. A control method of an X-ray imaging apparatus, comprising:
    reconstructing a plurality of volumes relating to an object, the plurality of volumes comprising:
        a first volume being generated based on an object area as a base of the volume and intensities of pixels in an X-ray image of the object as a first height;

a second volume being generated based on the object area as the base and intensities of pixels in a first reference image of the object as a second height, the first reference image being generated based on the object being of only adipose tissue; and a third volume being generated based on the object area as the base and intensities of pixels in a second reference image of the object as a third height, the second reference image being generated based on the object being of only fibroglandular tissue; and calculating a density of the object that is a ratio of fibroglandular tissue of the object with respect to entire tissue of the object, using the reconstructed first, second and third volumes, wherein the calculating the density comprises:

calculating the density based on a difference between the first volume of the object reconstructed front the X-ray image and the second volume of the object reconstructed from the first reference image.

12. The control method of claim 11, further comprising:

pressing the object using a pressure paddle disposed between an X-ray source assembly and an X-ray detection assembly;

producing the first reference image based on thickness information of the pressed object and an X-ray attenuation coefficient of adipose tissue; and producing the second reference image based on the thickness information of the pressed object and an X-ray attenuation coefficient of fibroglandular tissue.

13. The control method of claim 12, further comprising:

detecting a rotation angle of a driver configured to move the pressure paddle, using a rotation angle sensor; and calculating the thickness information of the pressed object based on the rotation angle detected by the rotation angle sensor.

14. The control method of claim 13, further comprising:

correcting the calculated thickness information based on a size of the object and a compression force applied to the object.

15. The control method of claim 14, wherein the size of the object is calculated based on a distance between a center point of an object area detected from the X-ray image, and a center point of the driver, and wherein the compression force applied to the object is detected by a compression force sensor disposed on a lower surface of the pressure paddle.

16. The control method of claim 12, further comprising:

detecting a distance to the pressure paddle, using a distance sensor array disposed in a lower portion of the X-ray source assembly; and calculating the thickness information of the pressed object based on the distance detected by the distance sensor array.

17. The control method of claim 12, wherein the reconstructing the first, second and third volumes relating to the object comprises:

reconstructing the first and second and third volumes relating to the object from the X-ray image, the first reference image, and the second reference image, respectively, based on the thickness information of the pressed object and information about radiography conditions of the X-ray image.

18. An X-ray imaging apparatus comprising:

an X-ray source assembly configured to generated and transmit an X-ray signal toward a breast;

an X-ray detection assembly configured to receive the X-ray signal that has propagated through the breast from the X-ray source assembly and output an electrical signal generated based on the received X-ray signal;

a controller configured to reconstruct a plurality of volumes relating to the beast and to calculate a density of the breast that is a ratio of fibroglandular tissue of the breast with respect to a total tissue of the breast using the reconstructed plurality of volumes, wherein the plurality of volumes comprises:

a first volume being generated based on a breast area as a base and intensities of pixels in an X-ray image of the breast as a first height;

a second volume being generated based on the breast area and intensities of pixels in a first reference image of the breast as a second height, the first reference image being generated based on the breast being of a single first material; and a third volume being generated based on the breast area and intensities of pixels in a second reference image of the breast as a third height, the second reference image being generated based on the breast being of a single second material different from the first material; and wherein the controller configured to calculate the density based on a difference between the first volume of the object reconstructed from the X-ray image and the second volume of the object reconstructed from the first reference image.

* * * * *